US006528636B1

(12) United States Patent
Gao et al.

(10) Patent No.: US 6,528,636 B1
(45) Date of Patent: Mar. 4, 2003

(54) PROMOTER SEQUENCE OF 3-PHOSPHOGLYCERATE KINASE GENE 2 OF LACTIC ACID-PRODUCING FUNGUS RHIZOPUS ORYZAE AND A METHOD OF EXPRESSING A GENE OF INTEREST IN FUNGAL SPECIES

(75) Inventors: Johnway Gao, Richland, WA (US); Rodney S. Skeen, Pendleton, OR (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/535,851

(22) Filed: Mar. 27, 2000

(51) Int. Cl.⁷ ................................................ C07H 21/04
(52) U.S. Cl. ...................... 536/24.1; 435/69.1; 435/471
(58) Field of Search ............................. 435/320.1, 69.1, 435/471; 536/24.1

(56) References Cited

FOREIGN PATENT DOCUMENTS

JP          3247286         * 11/1991

OTHER PUBLICATIONS

CR Soccol et al. "*Production of L–Lactic Acid by Rhizopus Species*", p. 433–435, 1994, vol. 10, World Journal Microbiol. Biotechnol.
MJ Haas et al. "*Cloning Expression and Characterization of a cDNA Encoding a Lipase From Rhizopus Delemar*", p. 107–113, 1991, Gene, vol. 109.
P Yin et al. "*Enhanced Production of L(+)–Lactic Acid Corn Starch in a Culture of Rhizopus Oryzae Using an Air–Lift Bioreactor*", p. 249–253. 1997 J. Fermentation and Bioengineering, vol. 84.
P Van Solingen et al. "*Sequence of the Penicillium Chrysogenum Phosphoglycerate Kinase Gene*", p. 11823, 1988 Nuc. Acids Res. vol. 16.
RA Hitzeman et al. "*The Primary Structure of the Saccharomyces Cerevisiae Gene for 3–Phosphoglycerate Kinase*", p. 7791–7808. 1982 Nuc. Acids Res. vol. 10.

N Takaya et al. "*Analysis of the 3–Phosphoglycerate Kinase 2 Promoter in Rhizopus Niveus*", p. 121–125. 1995 Gene, vol. 152.
S Vanhanen et al. "*Promoter Structure and Expression of the 3–Phosphoglycerate Kinase–Encoding Gene (pgkl) of Trichoderma Reesei*", p. 129–133. 1991. Gene, vol. 106.
MJ Haas et al. "*Lipases of the Genera Rhizopus and Rhizomucor: Versatile Catalysts in Nature and the Laboratory*", p. 549–588, 1994.
N Takaya et al. "*Cloning and Characterization of Two 3–Phosphoglycerate Kinase Genes of Rhizopus Niveus and Heterologous Gene Expression Using Their Promoters*", p. 524–530. 1994. Curr. Genet. vol. 25.
DJ Ballance. "*Transformation Systems for Filamentous Fungi and an Overview of Fungal Gene Structure*", p. 1–29. 1991.
MG Richey et al. "*Transformation of Filamentous Fungi with Plasmid DNA by Electroporation*", p. 844–847. 1989. Phytopathology vol. 79.
M Kapoor. "*Gene Transfer by Electroporation of Filamentous Fungi*", p. 279–289. 1996 in Methods in Molecular Biology, vol. 47.
MJ Holland et al. "*isolation and Identification of Yeast Messenger Ribonuclide Acids Coding for Enolase, Glyceraldehyde–3–Phosphate Dehydrogenase, and Phosphoglycerate Kinase*", p. 4900–4907. 1978 Biochemistry, vol. 17.
J Mellor et al. "*Efficient Synthesis of Enzymatically Active Calf Chymosin in Saccharomyces Cerevisiae*", p. 1–14. 1983 Gene, vol. 24.

* cited by examiner

Primary Examiner—Remy Yucel
Assistant Examiner—Bronwen M. Loeb
(74) Attorney, Agent, or Firm—Wells St. John P.S.

(57) ABSTRACT

The present invention provides the promoter clone discovery of phosphoglycerate kinase gene 2 of a lactic acid-producing filamentous fungal strain, *Rhizopus oryzae*. The isolated promoter can constitutively regulate gene expression under various carbohydrate conditions. In addition, the present invention also provides a design of an integration vector for the transformation of a foreign gene in *Rhizopus oryzae*.

11 Claims, 6 Drawing Sheets

| | | |
|---|---|---|
| 1 | gaattcattaaaacagaatgttcatgaatagattattctacttgtttcaatattgaaaaa | 60 |
| 61 | taaaagcagatatgatttaaaaggtgatgtaaaacatattagacttggttaacaattaaa | 120 |
| 121 | aactatacaagtagcatattaattagaaactcattgcattcattggtagttaaaatagaa | 180 |
| 181 | gcctcaatcaaatcaacaaaccaaatcttgtctcaacttttaacaatacattcatattta | 240 |
| 241 | aaaaaaatttatgcagatgattttttttttgggtcatgtattatttaacactccgaa | 300 |
| 301 | aataagaataaaatggttatcagagatgttatcagtgataccagaaatattgtactttcg | 360 |
| 361 | gtccttcttttttttttttccttgctctctttcttgttctttccatagtgtattgatt | 420 |
| 421 | taaaataagaagaaataaaatatgaaaaataagtcaagtctacagtagattgaatatct | 480 |
| 481 | tgtaagctactttacagaaacgcgttttctcagtttaatgaaatcccgcataacccatc | 540 |
| 541 | aagttgatcgtccaatggatgatcttggattttaaacttgcaaagtgaagtcatgattt | 600 |
| 601 | ttttttttttcgagaaattataacaattccaagtatctgttttttcttttcttttc | 660 |
| 661 | tttcaatcaacaaaaaATG | 679 |

*FIG. 3*

```
RNPGK2:   1                     tttaaaataaaagaataaataaaatacgaaaaataaaacaagt  43
                                |   |  || |  || | ||   ||| | ||||  |
ROPK38:395                      gtattgatttaaaataaagaagaaataaaatatgaaaaataag 454

RNPGK2: 44  tcaagtctacagtctattgaatatcttgtaagttactttacagaaacgcgttttctcagt 103
            ||||||||||||| |||||||||||||||||| ||||||||||||||||||||||||||
ROPK38:455  tcaagtctacagtagattgaatatcttgtaagctactttacagaaacgcgttttctcagt 514

RNPGK2:104  ttaatgaaattccgcataacccatcaagttgatcgtccaatagatgatcttggattttt 163
            ||||||||| ||||||||||||||||||||||||||||||| |||||||||||||||||
ROPK38:515  ttaatgaaatcccgcataacccatcaagttgatcgtccaatggatgatcttggattttt 574

RNPGK2:164  agacttgcaaagtgaagtcatgattttttttt-------cgagaaattataacaatacaag 216
            | |||||||||||||||||||||||||||||         ||||||||||||||||| | |
ROPK38:575  aaacttgcaaagtgaagtcatgattttttttttttttttcgagaaattataacaattccaa 634

RNPGK2:217  tgcgtgtctgtatttttttttt-ctttc-tttctttcaatcaac-aaaaATG 267
            |||| | |||||| ||||||  |||||||||||||||| |||||||
ROPK38:635  --------gtatctgtttttttctttctttttctttcaatcaacaaaaaaATG 679
```

FIG. 4

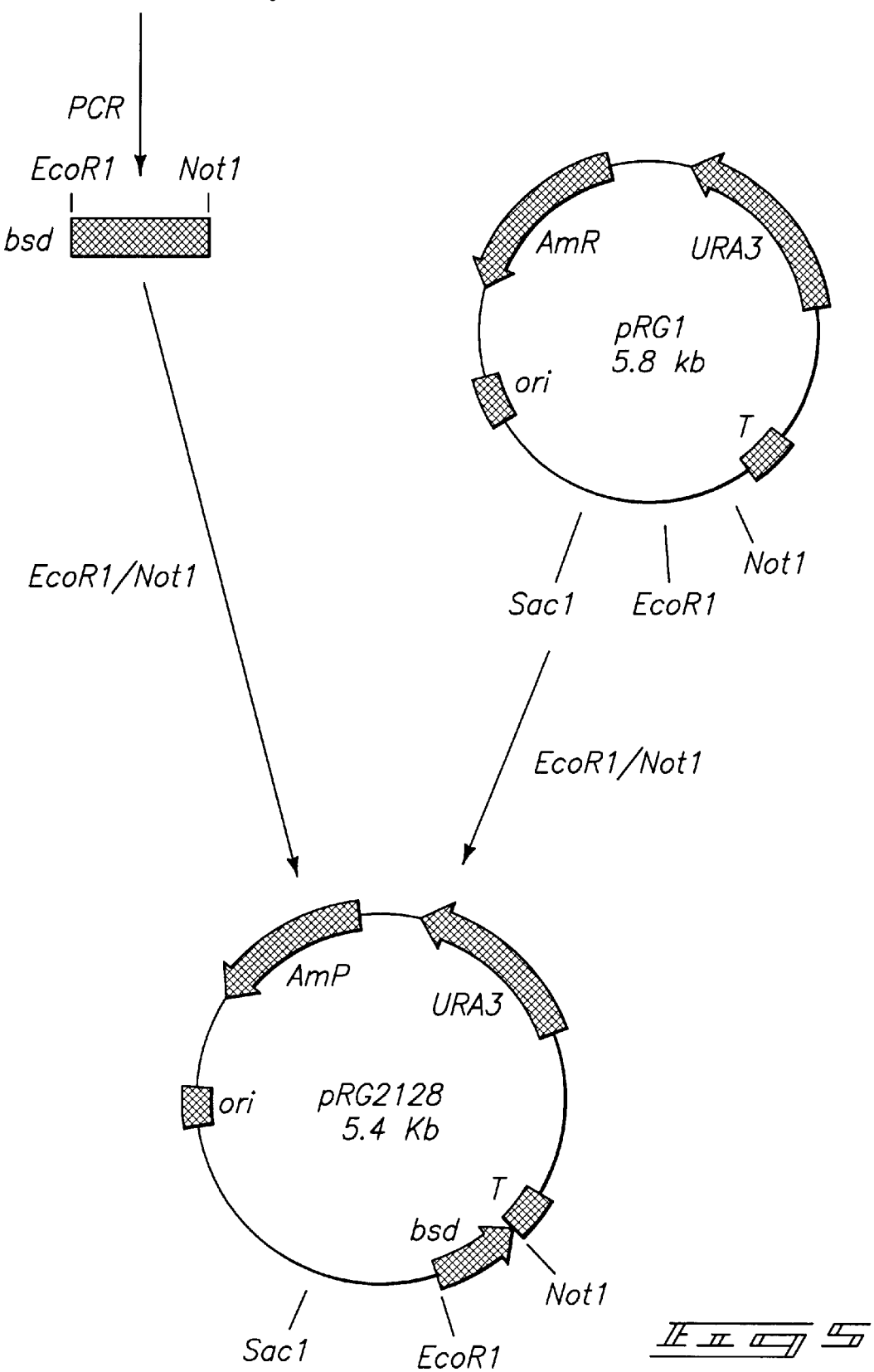

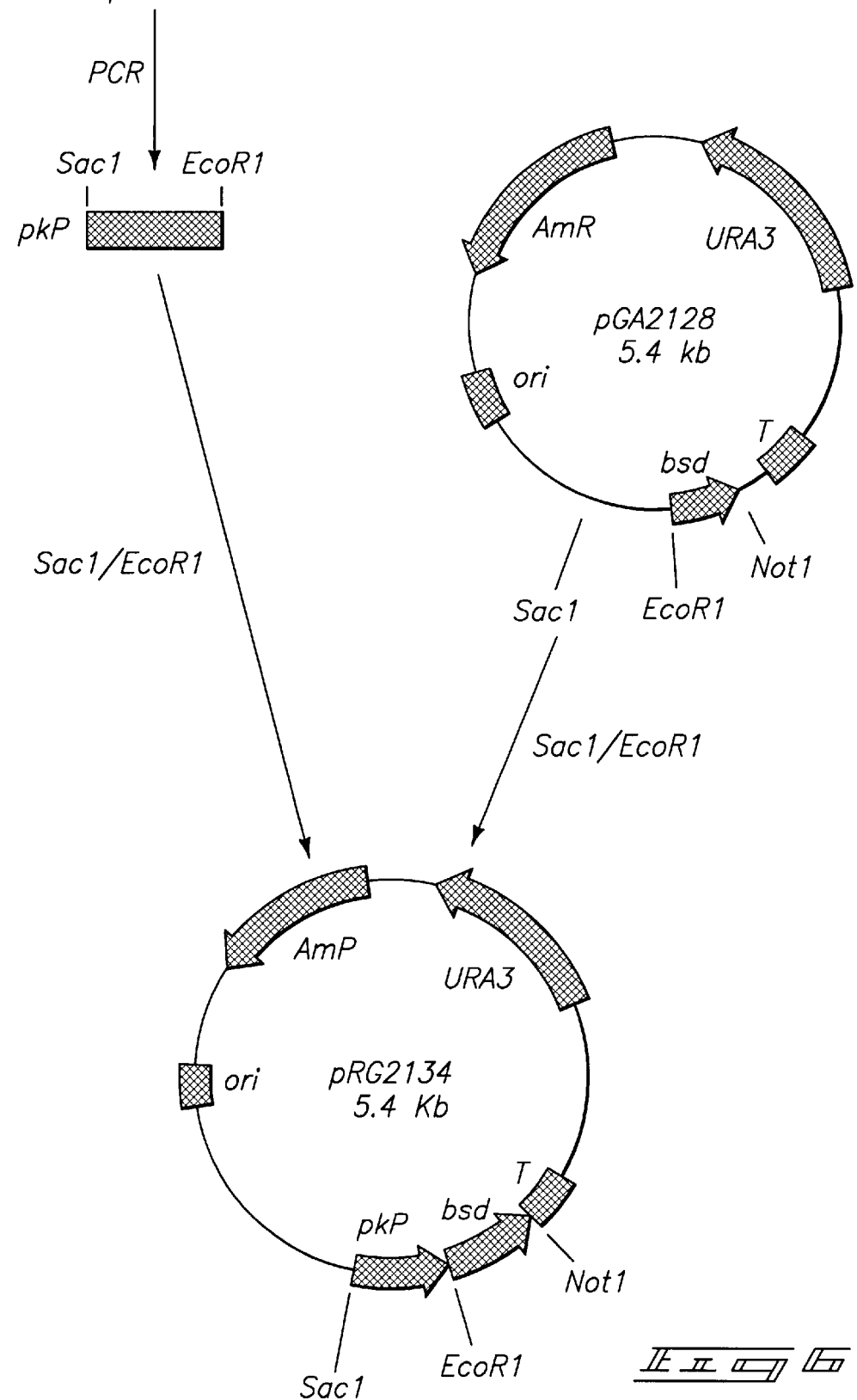

US 6,528,636 B1

PROMOTER SEQUENCE OF 3-PHOSPHOGLYCERATE KINASE GENE 2 OF LACTIC ACID-PRODUCING FUNGUS RHIZOPUS ORYZAE AND A METHOD OF EXPRESSING A GENE OF INTEREST IN FUNGAL SPECIES

This invention was made with Government support under Contract DE-AC0676RLO1830 awarded by the U.S. Department of Energy. The Government has certain rights in the invention.

FIELD OF THE INVENTION

The present invention is a promoter sequence of 3-phosphogycerate kinase gene 2 of lactic acid-producing fungus *Rhizopus oryzae* and a method of expressing a gene of interest in fungal species.

BACKGROUND OF THE INVENTION

The genus of Rhizopus is versatile in the production of biocatalysts such as glucoamylase and lipase and chemicals including L-(+)-lactic acid, fumaric acid, and ethanol. Rhizopus is the member of the order Mucorales, which is within the class Zygomycetes of the division Amastigomycota. *Rhizopus oryzae* (ATCC 9363) is the best lactic acid producer found in the Rhizopus genus, while *Rhizopus delemar* and *Rhizopus niveus* can produce significant amount of extracellular lipase. In addition, *R. oryzae* can also secrete large amount of glucoamylase in the solid culture for starch hydrolysis. Therefore, *R. oryzae* could be potentially a host for upgrading lactic acid production as well as foreign protein production. However, in the current literature, there is very limited information available on gene clones as well as gene regulatory elements (promoters) for *R. oryzae*. Less than nine gene clone and partial gene sequences are reported for *R. oryzae*, which include glucoamylase, ribosomal genes, and aspartic proteinase genes (GenBank Data Base).

The ability to genetically manipulate filamentous fungi largely depends on the successfulness to develop the transformation methods and gene expression systems. Transformation methods have been developed for filamentous fungi, in particular, *Aspergillus nidulans* and *Neurospora crassa*, including others such as *Aspergillus niger*, *Aspergillus oryzae*, *Penicillium nalgiovense*. To effectively direct the transcription or expression of an interested gene, strong gene regulating elements or promoters are required. These promoters can be isolated from the upstream sequences of strongly expressed gene clones. Phosphoglycerate kinase gene is one of the highly expressed genes found in yeast and filamentous fungi. This gene encodes some of the most abundant mRNA in the yeast cells, accounting for up to 5% of the total cellular protein expression. After the discovery and characterization of *Saccharomyces cerevisiae* gene, other phosphoglycerate kinase genes were also isolated from various fungal species such as *Penicillium chrysogenum* and *Rhizopus niveus* using *S. cerevisiae* phosphoglycerate kinase gene as homologous gene probe. However, only a few of phosphoglycerate kinase gene promoters were isolated and characterized, which were from *S. cerevisiae*, *Trichoderma reesei*, and *R. niveus*, among others.

To genetically manipulate *R. oryzae*, either for the purpose of metabolic pathway modification, conferring necessary traits such as acid tolerance and upgrading of lactic acid production, or producing biocatalyst of interest, high levels of mRNA expression are always desirable. Therefore, there is a need to isolate strong promoter sequences of *R. oryzae* and design/develop expression vectors, harboring the isolated phosphoglycerate kinase gene promoter.

SUMMARY OF THE INVENTION

The present invention provides the promoter clone discovery of phosphoglycerate kinase gene 2 of a lactic acid-producing filamentous fungal strain, *Rhizopus oryzae*. The isolated promoter can constitutively regulate gene expression under various carbohydrate conditions. In addition, the present invention also provides a design of an integration vector for the transformation of a foreign gene in *Rhizopus oryzae*.

BRIEF DESCRIPTION OF THE DRAWINGS

FIG. 3 is a graphic illustrating the sequence of a phosphoglycerate kinase 2 promoter of *R. oryzae*, SEQ ID NO: 7.

FIG. 4 is a graphic illustrating the homologous comparison of phosphoglycerate kinase 2 promoter sequences between *R. oryzae*, SEQ ID NO:9, and *R. niveus*, SEQ ID NO:8.

FIG. 5 is a graphic illustrating a plasmid vector pGA2128 construction.

FIG. 6 is a graphic illustrating a design of plasmid vector pGA2134 for *R. oryzae* transformation.

DESCRIPTION OF THE PREFERRED EMBODIMENT(S)

Figure 1:
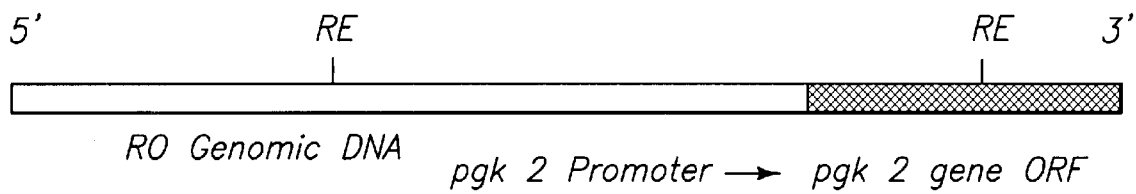
FIG. 1 is a graphic illustrating an inverse PCR method for phosphoglycerate kinase 2 promoter clone isolation.
Figure 1:
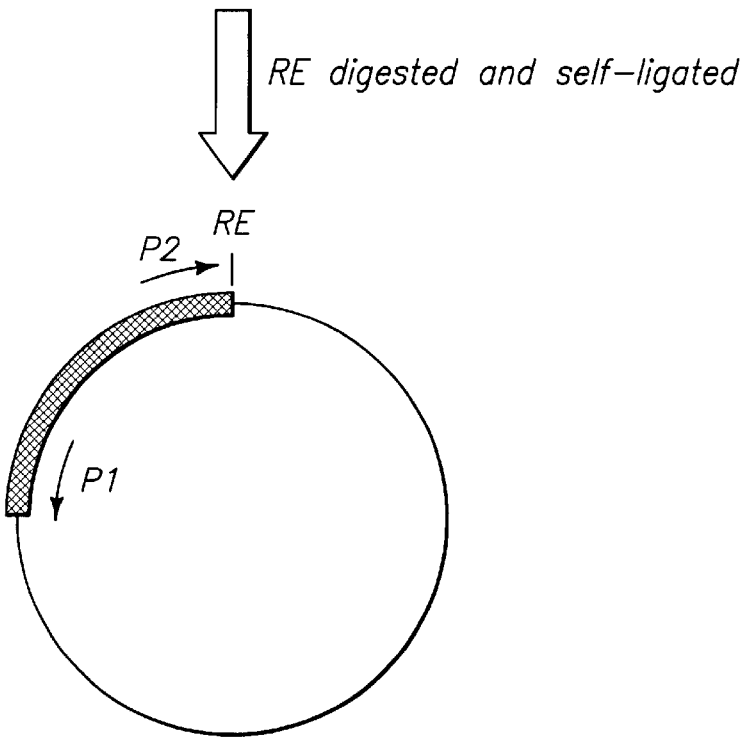
Figure 1:
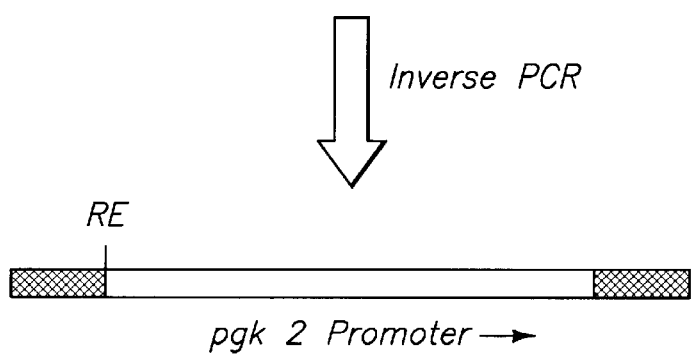

The present invention presents a promoter discovered in a fungal strain, *R. oryzae*, which is a lactic acid producing organism. The discovered promoter is related to the 3-phosphoglycerate kinase gene 2 (pgk2) promoter. The isolated promoter clone, SEQ ID NO: 7: has a length of 679 base pairs prior to the pgk2 gene initiation codon. As compared to the known upstream of *R. niveus* pgk2 gene sequence, SEQ ID NO: 8 from 1 to 267 base pairs, the *R. oryzae* pgk2 promoter sequence, SEQ ID NO: 9 from 395 to 679 base pairs has a significant difference of 55 base pairs, or 20.8% different prior to the initiation codon ATG. Both sequences diversified towards the 5' end at 43 base pair of *R. niveus*, and 454 base pair of *R. oryzae*, respectively. Furthermore, this invention presents a design of a transformation vector for the fungal strain, *R. oryzae*, which utilizes the native pgk2 promoter to regulate the antibiotic (blasticidin) resistance gene of *Aspergillus terreus* in *R. oryzae*. This vector can potentially be used as a chromosomal integration vector for other foreign gene expression in *R. oryzae*. Another objective of the current invention is to use the *R. oryzae* pgk2 promoter to regulate foreign gene expression in other fungal species and plants.

For a clear and concise understanding of the specification and claims, including the scope given to such terms, the following definitions are provided:

PROMOTER: The expression of a gene is directed by a promoter, which is a DNA sequence and locates in the 5' region of a gene. A fungal promoter is a promoter sequence that will direct the transcription of a gene in fungal cells.

CONSTITUTIVE PROMOTER: The rate of gene transcription under such promoter is not regulated by an inducing agent, which can be a chemical compound, or a carbohydrate.

INDUCIBLE PROMOTER: an inducing agent regulates the rate of gene transcription under such promoter.

PLASMID VECTOR: A DNA plasmid vector contains a replicon or an origin of replication able to autonomously replicate the plasmid DNA in the original host organism. A plasmid vector can also serve as both a cloning vector for DNA manipulation in a bacterial host and a shuttle plasmid vector for interested DNA expression in another host cell.

CLONING PLASMID VECTOR: Cloning vectors typically contain one or a small number of restriction endonuclease recognition sites at which interested DNA sequences can be inserted for DNA manipulation purposes. Cloning vectors also contain a marker gene that is suitable for use in the identification and selection of cells transformed with the cloning vector. Marker genes typically include genes that provide tetracycline resistance or ampicillin resistance.

SHUTTLE PLASMID VECTOR: Shuttle plasmid vectors are plasmid vectors that contain two replicons; one of which replicates plasmid vector in a bacterial host cell for DNA manipulation; and the other replicates plasmid vector in another host cell for gene expression. The shuttle plasmid vector typically contains two selectable marker genes; one of which is usually an ampicillin resistance gene or tetracycline resistance used for selection of cells transformed with the vector during DNA manipulation; and the other is usually an anti-fungal antibiotic resistance gene used for the selection of expression host cells transformed with the vector. A shuttle plasmid vector can also be an expression vector and normally contains an expression cassette (promoter//multiple cloning sites// transcription terminator) in which a gene of interest can be inserted.

CHROMOSOMAL INTEGRATION VECTOR: A chromosomal integration vector is a plasmid vector which is able to integrate the whole plasmid DNA or part of the interested DNA into the cell chromosomal DNA. The chromosomal integration is due to recombination of homologous DNA fragment into the cell chromosome by efficient DNA repairing mechanism during fungal transformation. A chromosomal integration vector can also be an expression vector and normally contains an expression cassette (promoter//multiple cloning sites//transcription terminator) in which a gene of interest can be inserted for gene expression or promoter characterization.

EXAMPLE 1

PCR cloning of phosphoglycerate kinase 2 promoter of *R. oryzae*.

To isolate the phosphoglycerate kinase 2 (pgk2) promoter from *R. oryzae* (ATCC 9363), the *R. oryzae* mycelium was grown overnight in a culture medium containing yeast extract 1%, peptone 2%, and potato starch 2%. Cells were then harvested and genomic DNA was isolated and purified from the culture. Inverse PCR method was used to clone out the promoter region, as shown in FIG. 1 where P1 is PCR reverse primer 1; P2 PCR forwarding primer 2; RE restriction enzyme site which can be cleaved both upstream of the pgk2 promoter and inside of the pgk2 gene; RO *Rhizopus oryzae*. PCR primers for the inverse PCR were designed based on the open reading frame of the pgk2 gene sequence of *Rhizopus niveus* under the assumption that pgk2 gene of *R. oryzae* and *R. niveus* is homologous. A 5' end over-hung sequence (italics) was designed to adapt restriction enzyme sites (underlined) such as Xba I and Sph I. The inverse PCR primers are listed as following:

Reverse primer PGK21-C-103; SEQ ID NO: 1:

GC *TCTAGA* TCA AGG TCA CGG ATA GAA AGT TTG TTA GAT

Reverse primer PGK22-C-104; SEQ ID NO: 2:

GC *TCTAGA* GTT GGT GAT AGC ACC ATC CTT CAT

Forwarding primer PGK23-N-105; SEQ ID NO: 3:

GAT *GCA TGC* CAA GTA CTC TCT TM GCC CGT TGC

Forwarding primer PGK24-N-106; SEQ ID NO: 4:

GAT *GCA TGC* TCT CAA CGT GCT GCT GGT TTC CTT ATG CA

Forwarding primer PGK25-N-107; SEQ ID NO: 5: GAT *GCA TGC* ATC GTC TGG AAC GGT CCC TCT GGT GTA Forwarding primer PGK26-N-108; SEQ ID NO: 6: GAT *GCA TGC* ATG TAT TTC ATA TTA ACT TGA ATA.

The genomic DNA is first digested with different restriction enzymes, including Ase I, BstB I, EcoR I, Hind III, Kpn I, Ssp I, Xho I, and Xmn I, which locate within the 5' region of the pgk2 gene of *R. niveus*. After digestion, the DNA samples are then purified and self-ligated using T4 DNA ligase. Table 1 shows the reverse PCR reaction matrix, which pairs various sets of reverse primer and forwarding primer together.

TABLE 1

Inverse PCR primer pair sets correspondent to each restriction enzyme digested DNA sample for the isolation of 3-phosphoglycerate kinase 2 promoter.

| PCR reaction No. | Restriction enzyme used before ligation | Inverse PCR primer pairing |
| --- | --- | --- |
| 1 | Ase I | PGK21-C-103; PGK21-C-106 |
| 2 | Ase I | PGK21-C-104; PGK21-C-106 |
| 3 | BstB I | PGK21-C-103; PGK21-C-107 |
| 4 | BstB I | PGK21-C-104; PGK21-C-107 |
| 5 | EcoR I | PGK21-C-103; PGK21-C-105 |
| 6 | EcoR I | PGK21-C-104; PGK21-C-105 |
| 7 | Hind III | PGK21-C-103; PGK21-C-105 |
| 8 | Hind III | PGK21-C-104; PGK21-C-105 |
| 9 | Kpn I | PGK21-C-103; PGK21-C-105 |
| 10 | Kpn I | PGK21-C-104; PGK21-C-105 |
| 11 | Ssp I | PGK21-C-103; PGK21-C-108 |
| 12 | Ssp I | PGK21-C-104; PGK21-C-108 |
| 13 | Xho I | PGK21-C-103; PGK21-C-106 |
| 14 | Xho I | PGK21-C-104; PGK21-C-106 |
| 15 | Xmn I | PGK21-C-103; PGK21-C-105 |
| 16 | Xmn I | PGK21-C-104; PGK21-C-105 |

Figure 2:
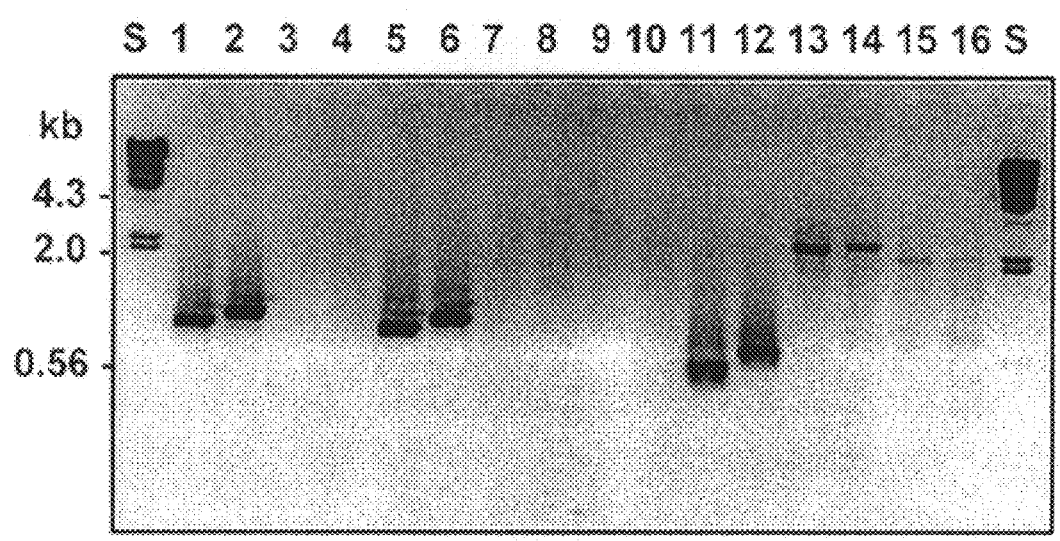
FIG. 2 is a reverse gel image of PCR clones of *R. oryzae* phosphoglycerate kinase 2 promoter.

The inverse PCR reactions were conducted based on the primer pairing outlined in Table 1. After PCR reaction, the PCR products were separated in an agarose gel by electrophoresis. The inverse PCR results are shown in a reverse gel image in FIG. 2, where lane number is correspondent to each inverse PCR reaction in Table 1 and lane Hλ is the DNA size marker. The isolated pgk2 promoter clones are indicated as dark bands in the gel picture. Lanes 1, 2, 5, 6, 11, 12, 13, and 14 show strong bands, which correspondent to the ligated DNA samples previously cleaved by Ase I, EcoR I, SspI, and Xho I, respectively. The sizes of the PCR clones range from about 0.5 kb to 2.5 kb.

EXAMPLE 2

Nucleotide sequence of pgk2 promoter sequence.

PCR product No. 5 has a size of about 0.7 kb, which was prepared by the restriction enzyme EcoR I locating close to the initial codon ATG. The other PCR products prepared by Ase I restriction enzyme has the same size as the one prepare by EcoR I while the one prepared by Ssp I has a size of about 0.6 kb and the one prepared by Xho I has a size of about 2.5 kb. The pgk2 promoter clone No. 5 was cloned into a vector pGEM-T (Promega, Madison, WIS.) to form pGA2088. Individual colonies were picked to confirm DNA insertion. Two of the individual clones, pGA2088a and pGA2088b, were completely sequenced from both ends. By sequence blasting, the overlapping sequence of these two clones indicated that they are identical and belong to one gene sequence. The complete nucleotide sequence of pgk2 gene promoter is shown in FIG. 3; SEQ ID NO: 7. The cloned pgk2 promoter sequence has a length of 679 bp. The putative TATA box and CAT box are bold and underlined. There are three CAT boxes and one TATA box within 200 base pairs upstream of the initial codon.

EXAMPLE 3

Homologous comparison of pgk2 promoter sequence between R. oryzae and R. niveus.

To compare the homology of pgk2 promoter between R. oryzae and R. niveus, promoter sequences from both origins were blasted against each other. The comparison results of pgk2 promoter are shown in FIG. 4, where ROPK38 is R. oryzae pgk2 promoter sequence, SEQ ID NO: 9; RNPGK2 is R. niveus pgk2 promoter sequence, SEQ ID NO: 8. The bold letters indicate the difference of both sequences and "–" indicates missing nucleotides of both sequences. ATG is the putative initial codon of pgk2 gene. When compared to the known upstream of R. niveus pgk2 gene sequence from 1 to 267 base pairs, the R. oryzae pgk2 promoter sequence from 395 to 679 base pairs has a difference of 55 base pairs, or 20.8% different prior to the initiation codon ATG of the pgk2 gene. Both sequences diversified towards the 5' end at 43 base pair of R. niveus, and 454 base pair of R. oryzae, respectively. These results conclude that the pgk2 promoter sequences of R. oryzae are not identical to the one isolated from R. niveus (Takaya et al., 1994), even though they are highly homologous.

EXAMPLE 4

Transformation vector design and construction for R. oryzae.

To develop transformation vector system for foreign gene expression in R. oryzae, the following vector was designed. A blasticidin resistance gene (Invitrogen, Carlsbad, CA) was first cloned out by PCR, and cloned into pGEM-T vector (Promega, Madison, WIS.) to adapt EcoR I at the 5' end of the gene and Not I site at the 3' end, forming a plasmid vector pGA2125. The blasticidin gene was subsequently cloned into a vector pRG1 as shown in FIG. 5, forming plasmid pGA2128. Plasmid vector pRG2134 for gene expression and integration in R, oryzae was then constructed and is shown in FIG. 6, where AmR: ampicillin resistance gene; bsd: antibiotic blasticidin resistance gene; ori: Col El origin; T: fungal transcription terminator TAOXI; pk P: R. oryzae pgk2 promoter; and URA3: Pichia pastoris orotidine-5'-phosphate decarboxylase gene. The selectable marker gene provides R. oryzae with resistance to antibiotics, blasticidin. Other antibiotic resistance genes such as sulfanilamide and Gentamycin resistance genes can replace the blasticidin selectable marker gene. The selectable marker gene is placed under the control of R. oryzae pgk2 promoter and a fungal transcription terminator, TAOX1, terminates the transcription. In addition, a heterogenous or homogenous URA3 gene or other native gene sequences can be used as integration elements for chromosomal gene insertion. Besides, pgk2 promoter sequence can potentially serve as chromosomal integration elements. Chromosomal integration vectors incorporate the desired gene into cell chromosome based on the underlying principle that linearized plasmid DNA fragments are efficiently repaired during fungal transformation by recombination with a homologous DNA restriction fragments.

CLOSURE

While preferred embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An isolated phosphoglycerate kinase gene 2 (pgk2) promoter comprising at least nucleotides 395–676 of SEQ ID No.:7.

2. The isolated pgk2 promoter of claim 1, wherein said promoter comprises the first 676 base pairs of SEQ ID No.:7.

3. A vector comprising the isolated pgk2 promoter of claim 1.

4. The vector of claim 3, whereby the vector is a plasmid vector.

5. The vector of claim 4, whereby the plasmid vector is a chromosomal integration vector.

6. A process of regulating the expression of a gene, comprising the steps of:
   a. providing a coding region that encodes a gene product;
   b. fusing the coding region to the isolated pgk2 promoter of claim 1 to form a fused promoter/coding region; and
   c. integrating the fused promoter/coding region within a genomic DNA in cells wherein the promoter regulates the expression of the gene product in the cells.

7. The process of regulating the expression of a gene product of claim 6 wherein the genomic DNA comprises fungal genomic DNA and wherein the cells comprise fungal cells.

8. The process of regulating the expression of a gene product of claim 6 wherein the genomic DNA comprises plant genomic DNA and wherein the cells comprise plant cells.

9. The process of regulating the expression of a gene product of claim 7 wherein the fungal genomic DNA comprises *Rhizopus oryzae* genomic DNA and wherein the fungal cells comprise *Rhizopus oryzae* cells.

10. A process of regulating the expression of a gene, comprising the steps of:
    a. providing a coding region that encodes a gene product;
    b. fusing the coding region to the isolated pgk2 promoter of claim 1 to form a fused promoter/coding region;
    c. constructing a plasmid vector comprising said fused promoter/coding region; and
    d. replicating said plasmid vector within a fungal cell such that the fungal promoter regulates the expression of the gene product in the fungal cell.

11. The process of regulating the expression of a gene product of claim 10 wherein the fungal genomic DNA comprises *Rhizopus oryzae* genomic DNA and wherein the fungal cells comprise *Rhizopus oryzae* cells.

* * * * *

UNITED STATES PATENT AND TRADEMARK OFFICE
CERTIFICATE OF CORRECTION

PATENT NO.    : 6,528,636 B1
DATED         : March 4, 2003
INVENTOR(S)   : Gao et al.

It is certified that error appears in the above-identified patent and that said Letters Patent is hereby corrected as shown below:

Column 4,
Lines 2 and 6, reaplace "*TCT AGA*" with -- *TCT AGA* --.
Line 10, replace "*GCA TGC*" with -- *GCA TGC* --.
Line 10, replace "TM" with -- TAA --.
Lines 11, 14 and 16, replace "*GCA TGC*" with -- *GCA TGC* --.
Line 57, replace "SspI" with -- Ssp I --.

Column 6,
Line 13, replace "R, *oryzae*" with -- R. *oryzae* --.
Lines 16 and 25, replace "TAOXI" with -- $T_{AOX1}$ --.

Signed and Sealed this

Nineteenth Day of August, 2003

JAMES E. ROGAN
*Director of the United States Patent and Trademark Office*

SEQUENCE LISTING

<160> NUMBER OF SEQ ID NOS: 9

<210> SEQ ID NO 1
<211> LENGTH: 38
<212> TYPE: DNA
<213> ORGANISM: artificial sequence
<220> FEATURE:
<223> OTHER INFORMATION: oligonucleotide primer

<400> SEQUENCE: 1
gctctagatc aaggtcacgg atagaaagtt tgttagat                38

<210> SEQ ID NO 2
<211> LENGTH: 32
<212> TYPE: DNA
<213> ORGANISM: Artificial Sequence
<220> FEATURE:
<223> OTHER INFORMATION: oligonucleotide primer -continued

<400> SEQUENCE: 2
gctctagagt tggtgatagc accatccttc at                                    32

<210> SEQ ID NO 3
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 3
gatgcatgcc aagtactctc ttaagcccgt tgc                                   33

<210> SEQ ID NO 4
<211> LENGTH: 38
<212> TYPE: DNA
<213> ORGANISM: Artificial Sequence
<220> FEATURE:
<223> OTHER INFORMATION: oligonucleotide primer

<400> SEQUENCE: 4
gatgcatgct ctcaacgtgc tgctggtttc cttatgca                              38

<210> SEQ ID NO 5
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 5
gatgcatgca tcgtctggaa cggtccctct ggtgta                                36

<210> SEQ ID NO 6
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 6
gatgcatgca tgtatttcat attaacttga ata                                   33

<210> SEQ ID NO 7
<211> LENGTH: 679
<212> TYPE: DNA
<213> ORGANISM: Rhizopus Oryzae

<400> SEQUENCE: 7
gaattcatta aaacagaatg ttcatgaata gattattcta cttgtttcaa tattgaaaaa       60
taaaagcaga tatgatttaa aaggtgatgt aaaacatatt agacttggtt aacaattaaa      120
aactatacaa gtagcatatt aattagaaac tcattgcatt cattggtagt aaaatagaa       180 gcctcaatca aatcaacaaa ccaaatcttg tctcaacttt taacaataca ttcatattta      240
aaaaaaaatt tatgcagatg attttttttt tttgggtcat gtattattta acactccgaa      300
aataagaata aatggttat cagagatgtt atcagtgata ccagaaatat tgtactttcg       360
gtccttcttt tttttttttt tccttgctct ctttcttgtt cttccatag tgtattgatt       420 taaaataaag aagaaataaa atatgaaaaa taagtcaagt ctacagtaga ttgaatatct      480
tgtaagctac tttacagaaa cgcgtttct cagtttaatg aaatcccgca taaccccatc      540

-continued

```
aagttgatcg tccaatggat gatcttggat ttttaaactt gcaaagtgaa gtcatgattt        600
tttttttttt ttcgagaaat tataacaatt ccaagtatct gttttttct tttcttttc          660 tttcaatcaa caaaaaatg                                                     679
```

<210> SEQ ID NO 8
<211> LENGTH: 267
<212> TYPE: DNA
<213> ORGANISM: Rhizopus niveus

<400> SEQUENCE: 8

```
tttaaaataa aagaataaat aaaatacgaa aaataaaaca agttcaagtc tacagtctat         60
tgaatatctt gtaagttact ttacagaaac gcgttttctc agtttaatga aattccgcat       120
aaccccatca agttgatcgt ccaatagatg atcttggatt tttagacttg caaagtgaag       180
tcatgatttt ttttcgagaa attataacaa tacaagtgcg tgtctgtatt ttttttttct      240
tttcttttct ttcaatcaac aaaaatg                                           267
```

<210> SEQ ID NO 9
<211> LENGTH: 268
<212> TYPE: DNA
<213> ORGANISM: Rhizopus oryzae

<400> SEQUENCE: 9

```
gtattgattt aaaataaaga agaaataaaa tatgaaaaat aagtcaagtc tacagtagat         60
tgaatatctt gtaagctact ttacagaaac gcgttttctc agtttaatga aatcccgcat       120
aaccccatca agttgatcgt ccaatggatg atcttggatt tttaaacttg caaagtgaag       180
tcatgatttt ttttttttt tcgagaaatt ataacaattc caagtatctg ttttttctt         240 ttcttttct ttcaatcaac aaaaaatg                                           268
```